United States Patent
Hommeltoft et al.

(10) Patent No.: US 9,040,752 B2
(45) Date of Patent: May 26, 2015

(54) PROCESS FOR PRODUCING KETONES FROM FATTY ACIDS

(75) Inventors: Sven Ivar Hommeltoft, Pleasant Hill, CA (US); Ann Jia-Bao Liang, Walnut Creek, CA (US)

(73) Assignee: Chevron U.S.A. Inc., San Ramon, CA (US)

( * ) Notice: Subject to any disclaimer, the term of this patent is extended or adjusted under 35 U.S.C. 154(b) by 409 days.

(21) Appl. No.: 13/486,097

(22) Filed: Jun. 1, 2012

(65) Prior Publication Data

US 2013/0324449 A1   Dec. 5, 2013

(51) Int. Cl.
*C07C 45/41* (2006.01)
*C10M 105/20* (2006.01)

(52) U.S. Cl.
CPC .............. *C10M 105/20* (2013.01); *C07C 45/41* (2013.01); *C10M 2207/085* (2013.01); *C10N 2280/00* (2013.01)

(58) Field of Classification Search
CPC ..... C07C 45/48; C07C 1/20; C10M 2207/085
USPC .......................................... 568/397; 508/577
See application file for complete search history.

(56) References Cited

U.S. PATENT DOCUMENTS

| | | | |
|---|---|---|---|
| 3,852,207 | A | 12/1974 | Stangeland et al. |
| 4,673,487 | A | 6/1987 | Miller |
| 5,135,638 | A | 8/1992 | Miller et al. |
| 5,282,958 | A | 2/1994 | Santilli et al. |
| 7,282,134 | B2 | 10/2007 | Abernathy et al. |
| 7,501,546 | B2 | 3/2009 | Koivusalmi et al. |
| 7,795,484 | B2 | 9/2010 | Koivusalmi et al. |
| 7,850,841 | B2 | 12/2010 | Koivusalmi et al. |
| 7,888,542 | B2 | 2/2011 | Koivusalmi et al. |
| 7,967,973 | B2 | 6/2011 | Myllyoja et al. |
| 7,998,339 | B2 | 8/2011 | Myllyoja et al. |
| 8,048,290 | B2 | 11/2011 | Knuuttila et al. |
| 2009/0285728 | A1 | 11/2009 | Miller |

OTHER PUBLICATIONS

U.S. Appl. No. 13/157,921, filed Jun. 10, 2011, Bi-Zeng Zhan et al., "Conversion of Fatty Acids to Base Oils and Transportation Fuels".
C.A. Gaertner et al., Catalytic Coupling of Carboxylic Acids by Ketonization as a Processing Step in Biomass Conversion, *Journal of Catalysis*, 266, (2009), pp. 71-78.
M. Glinski et al., Catalytic Ketonization of Carboxylic Acids Synthesis of Saturated and Unsaturated Ketones, *React. Kinet. Catal. Lett.*, vol. 69, No. 1, pp. 123-128, (2000).
Xiong et al., A Bio-Catalytic Approach to Aliphatic Ketones, *Science Reports*, 2, 311, pp. 1-7, Mar. 13, 2012.
Vogel's Textbook of Practical Organic Chemistry, Forth edition, Longman New York 1978, pp. 429-433.
Anneken, D. J., Both, S., Christoph, R., Fieg, G., Steinberner, U. and Westfechtel, A., 2006, Fatty Acids. Ullmann's Encyclopedia of Industrial Chemistry, vol. 14, 5th ed., pp. 73-112; VCH: Weinheim, Germany, at p. 79, Fig. 7.

*Primary Examiner* — Sikarl Witherspoon
(74) *Attorney, Agent, or Firm* — Melissa M. Hayworth; Steven H. Roth

(57) ABSTRACT

The invention relates to a process for producing ketones or hydrocarbon base oil from fatty acids preferably derived from a biological origin or other renewable source. The process is directed at making an aliphatic ketone or a mixture of aliphatic ketones having 14 to 52 carbon atoms, comprising a ketonization reaction of a fatty acid in a vapor phase with a decarboxylation-coupling catalyst to provide ketones, which can be deoxygenated to give saturated hydrocarbons, unsaturated hydrocarbons, and mixtures thereof. Base oils and transportation fuels may be produced from the process herein.

13 Claims, No Drawings

PROCESS FOR PRODUCING KETONES FROM FATTY ACIDS

FIELD OF THE INVENTION

The application relates to processes for making aliphatic ketone or a mixture of aliphatic ketones by means of a vapor phase coupling of fatty acids.

BACKGROUND OF THE INVENTION

There are numerous efforts underway to generate hydrocarbon base oils from renewable biomass. (e.g., Xiong et al., A Bio-Catalytic Approach to Aliphatic Ketones, *Science Reports*, 2, 311, pp. 1-7, Mar. 13, 2012). One approach is to generate aliphatic ketones from fatty acids or their derivatives. The aliphatic ketone or mixture of aliphatic ketones produced can then be deoxygenated to give saturated hydrocarbons.

The preparation of ketones from carboxylic acids is well known and has been used in the preparation of ketones from carboxylic acids for many years. (e.g., Vogel's Textbook of Practical Organic Chemistry, Forth edition, Longman N.Y. 1978, pp. 429-433). It is also well known that the reactions can be used to convert fatty acids such as stearic acid and other fatty acids of natural origin to ketones in the base oil boiling range. (e.g., U.S. patent application Ser. No. 13/157,921; and U.S. Pat. Nos. 7,850,841; 7,967,973; and 8,048,290). Conventional ketonization operates at high temperatures (e.g., ≥300° C.) and can produce significant amounts of by-products such as light fragments formed in various ways such as by cracking of the fatty acid chains or by decarboxylation of the fatty acid. The formation of these by-products limits the overall selectivity and thus the yield of the desired ketone product. There has so far been a limited understanding of the factors that causes the relatively poor selectivity. In addition, the side reactions that cause the lower selectivity also tend to cause faster catalyst passivation.

We have discovered that the selectivity in the reaction of fatty acids to form ketones is dependent on the partial pressure of the fatty acids. Intuitively one might have expected that a condensation reaction such as the reaction of two molecules of fatty acid to form one molecule of ketone would be favored by higher partial pressure of the reactants, but to our surprise we have observed that the opposite is the case. We have found that the ketone selectivity and the catalyst stability is favored by low partial pressure of the fatty acids. In fact, it proves to be of critical importance to the selectivity that the partial pressure of the fatty acid in the reactor is kept below the pressure at which the fatty acid could condense into a liquid phase at the reaction temperature.

SUMMARY OF THE INVENTION

In one embodiment, the present invention provides a process for making an aliphatic ketone or a mixture of aliphatic ketones having about 14 to 52 carbon atoms, comprising: reaction of a fatty acid in a vapor phase with a decarboxylation-coupling catalyst in a decarboxylation-coupling zone, wherein a decarboxylation-coupling zone temperature is between about 20° C. to 100° C. above the condensation point of the fatty acid at the partial pressure of the fatty acid in the decarboxylation-coupling zone.

In yet another embodiment, the present invention provides a process for making an aliphatic ketone or a mixture of aliphatic ketones having about 14 to 52 carbon atoms, comprising: reaction of a fatty acid in a vapor phase with a decarboxylation-coupling catalyst in a decarboxylation-coupling zone, wherein a partial pressure of the fatty acid is between about 1% to 90% of the partial pressure at the condensation point at a given decarboxylation-coupling zone temperature.

DETAILED DESCRIPTION OF THE INVENTION

In some embodiments, the present invention provides a process for making an aliphatic ketone or a mixture of aliphatic ketones having about 20 to 48 carbon atoms.

In some embodiments, the present invention provides a process for making an aliphatic ketone or a mixture of aliphatic ketones having 20, 21, 22, 23, 24, 25, 26, 27, 28, 29, 30, 31, 32, 33, 34, 35, 36, 37, 38, 39, 40, 41, 42, 43, 44, 45, 46, 47, 48 carbon atoms, and combinations thereof.

In some embodiments, the decarboxylation-coupling zone temperature is between about 20° C. to 75° C. above the condensation point of the fatty acid at the partial pressure of the fatty acid in the decarboxylation-coupling zone.

In some embodiments, the decarboxylation-coupling zone temperature is at least about 20° C., 25° C., 30° C., 35° C., 40° C., 45° C., 50° C., 55° C., 60° C. or 65° C. above the condensation point of the fatty acid at the partial pressure of the fatty acid in the decarboxylation-coupling zone.

In some embodiments, the decarboxylation-coupling zone temperature is at least about 27° C. above the condensation point of the fatty acid at the partial pressure of the fatty acid in the decarboxylation-coupling zone.

In some embodiments, the decarboxylation-coupling zone pressure is between about 200 psia to 1 psia.

In some embodiments, the decarboxylation-coupling zone pressure is equal to or less than about 200 psia, 100 psia, 50 psia, 20 psia, atmospheric pressure, 10 psia, 5 psia or 2 psia.

In some embodiments, the decarboxylation-coupling zone pressure is between about 200 psig to 1 psig.

In some embodiments, the decarboxylation-coupling zone pressure is equal to or less than about 200 psig, 100 psig, 75 psig, 50 psig, 40 psig, 25 psig, atmospheric pressure, 10 psig, 5 psig or 2 psig.

In some embodiments, the decarboxylation-coupling zone pressure is between about 200 psi to 1 psi.

In some embodiments, the decarboxylation-coupling zone pressure is equal to or less than about 200 psi, 150 psi, 100 psi, 75 psi, 50 psi, 40 psi, 25 psi, atmospheric pressure, 10 psi, 5 psi or 2 psi.

In some embodiments, the present invention provides a partial pressure of the fatty acid is maintained at between about 100 psia to 1 psia.

In some embodiments, the present invention provides a partial pressure of the fatty acid is maintained at between about 75 psia to 1 psia.

In some embodiments, the present invention provides a partial pressure of the fatty acid is maintained at between about 50 psia to 1 psia.

In some embodiments, the present invention provides a partial pressure of the fatty acid is maintained at less than about 30 psia, 20 psia or atmospheric.

In some embodiments, the present invention provides a partial pressure of the fatty acid is maintained at no more than about 15 psia, 10 psia, 9 psia, 8 psia, 7 psia, 6 psia, 5 psia, 4 psia, 3 psia or 2 psia.

In some embodiments, the decarboxylation-coupling zone temperature is between about 100° C. to 500° C., 200° C. to 500° C., 300° C. to 500° C., 400° C. to 500° C., 300° C. to 400° C. or 360° C. to 427° C.

In some embodiments, the partial pressure of the fatty acid is maintained at no more than about 90%, 75%, 50%, 25%, 10%, 5% or 2% of a partial pressure at the condensation point at a given decarboxylation-coupling zone temperature.

In some embodiments, the partial pressure of the fatty acid is controlled with the addition of an inert diluent selected from the group consisting of nitrogen, hydrogen, carbon monoxide, water, carbon dioxide, $C_1$-$C_{18}$ aliphatic hydrocarbon, and mixtures thereof.

In some embodiments, the partial pressure of the fatty acid is controlled by lowering the pressure under vacuum.

In some embodiments, the decarboxylation-coupling catalyst is selected from the group consisting of alumina, supported metal carbonates, supported metal hydroxides, supported metal oxides, and combinations thereof.

In some embodiments, the fatty acid is selected from the group consisting of caproic acid, caprylic acid, capric acid, lauric acid, myristic acid, palmitic acid, stearic acid, arachidic acid, palm kernel oil acid, palm oil acid, coconut oil acid, soy bean oil acid, rape seed oil fatty acid, poultry fat derived fatty acids, beef tallow derived fatty acids, and combinations thereof.

In some embodiments, the present invention provides a fatty acid conversion to the ketone of between about 70% to 100%.

In some embodiments, the present invention provides a fatty acid conversion to the ketone of at least about 75%, 80%, 90% or 95%.

In some embodiments, the present invention provides a fatty acid conversion selectivity to the ketone of between about 30% to 100%.

In some embodiments, the present invention provides a fatty acid conversion selectivity to the ketone of at least about 30%, 40%, 50%, 60%, 70%, 80%, 90% or 95%.

In some embodiments, the present invention provides process whereby the ketones produced can then be deoxygenated to give saturated hydrocarbons.

In some embodiments, the present invention provides a process for making saturated aliphatic ketones, unsaturated aliphatic ketones, and combinations thereof.

In some embodiments, the saturated and unsaturated hydrocarbon produced has a viscosity index of between about 120 to 200.

In some embodiments, the saturated and unsaturated hydrocarbon produced has a viscosity index of at least about 120, typically at least about 140, and often at least about 160.

In some embodiments, the saturated and unsaturated hydrocarbon produced has a pour point of between about 0° C. to −70° C.

In some embodiments, the saturated and unsaturated hydrocarbon produced has a pour point of less than about 0° C., −20° C., −30° C., −40° C., −50° C. or −60° C.

In some embodiments, the present invention provides a process further comprising a step of distilling, hydrocracking, hydroisomerization dewaxing, hydrofinishing, and combinations thereof.

In some embodiments, the present invention provides a process further comprising a step of flash distillation.

In some embodiments, the present invention provides a process further comprising a step of blending the saturated and unsaturated hydrocarbon produced with a base oil selected from the group consisting of Group I base oils, Group II base oils, Group III base oils, and combinations thereof.

I. Fatty Acid Feed

The feed stock comprises at least one fatty acid or a mixture of fatty acids. The feedstock is typically derived from a triglyceride-containing biomass source such as plant, vegetable, animal and fish oils and fats. It will be further appreciated that some such sources are more economical and more amenable to regional cultivation, and also that those sources from which food is not derived may be additionally attractive. The biomass source can be treated using any pre-treatment or purification method well known in the art to obtain fatty acids useful as the feedstock, such as hydrolysis. Those of skill in the art will recognize that the types and lengths of the fatty acids are dependent upon the biomass source from which they are derived.

In some embodiments, the fatty acid feedstock is derived from other non-biomass sources (e.g., Fischer-Tropsch synthesis). Such alternatively-derived fatty acids could be mixed with the biomass-derived fatty acid prior to ketonization. Such mixing could serve to alleviate logistical and/or supply related issues involving biomass.

The fatty acid feed can be a bio-derived fatty acid formed by hydrolysis of one or more triglyceride-containing vegetable oils such as, but not limited to, coconut oil, corn oil, linseed oil, olive oil, palm oil, palm kernel oil, rapeseed oil, safflower oil, soybean oil, sunflower oil, and the like. Moreover, additional sources of triglycerides, which can be hydrolyzed to yield fatty acids, include, but are not limited to, algae, animal tallow and zooplankton.

The carbon lengths of suitable of saturated fatty acids such as, but not limited to, caproic acid ($C_6$), caprylic acid ($C_8$), capric acid ($C_{10}$), lauric acid ($C_{12}$), myristic acid ($C_{14}$), palmitic acid ($C_{16}$), stearic acid ($C_{18}$), arachidic acid ($C_{20}$). The carbon lengths of suitable of unsaturated fatty acids includes, but not limited to, $C_8$-$C_{22}$ fatty acids, and combinations thereof. Examples of unsaturated acids are palmitoleic acid, oleic acid and Linoleic acid.

Also mixtures from various natural resources are suitable feed stocks. Examples of these are palm kernel oil acids (a mixture of $C_8$ to $C_{22}$ fatty acids, primarily lauric acid and myristic acid), coconut oil acid (a mixture of $C_8$ to $C_{22}$ fatty acids, primarily lauric acid and myristic acid), palm oil acids, soy bean oil acids, rape seed oil fatty acids, poultry fat derived fatty acids, beef tallow derived fatty acids, and combinations thereof.

In some aspects, wherein the above-mentioned hydrolyzed triglyceride sources contain mixtures of saturated fatty acids, mono-unsaturated fatty acids, and polyunsaturated fatty acids, one or more techniques may be employed to isolate, concentrate, or otherwise separate the desired fatty acids from the other fatty acids in the mixture (e.g., U.S. Patent Application Publication No. 2009/0285728).

II. Decarboxylation-Coupling

Ketones may be prepared by decarboxylation-coupling of fatty acids. Without wishing to be bound by any particular theory, a ketone is formed in the decarboxylation-coupling process from two moles of fatty acid. Carbon dioxide and water are produced as by-products. The following illustrates this proposed reaction scheme:

Scheme 1

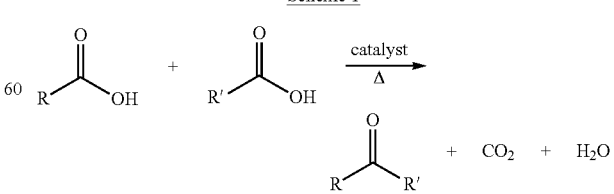

Wherein, R and R' are saturated or unsaturated aliphatic and can be the same or different.

III. Process Conditions

Suitable ketonization conditions may include a temperature of from 100° C. to 500° C. or from 300° C. and 450° C.; a pressure from no more than 200 psia, 100 psia, 50 psia, 20 psia, atmospheric pressure, 10 psia, 5 psia or 2 psia; and a liquid hourly space velocity (LHSV) of from 0.1 to 50 h$^{-1}$ or from 0.5 to 10 h$^{-1}$. Furthermore, the partial pressure of the fatty acid is maintained at less than atmospheric and no more than 10 psia, 5 psia or 2 psia.

Suitable catalysts for fatty acid decarboxylation-coupling include alumina, supported metal carbonates, supported metal hydroxides, supported metal oxides, or combinations thereof. Typical metals include, but not limited to, Mg, Ca, Sr, Ba, Th and Mn. The support for metal carbonates or hydroxides can be chosen from any refractory material such as alumina, silica, silica-alumina, titania, zirconia, zinc oxide, magnesium oxide, and combinations thereof, or even naturally-occurring materials such as pumice.

The decarboxylation-coupling process can be carried out in batch or continuous mode, with recycling of unconsumed starting materials if required.

Ketones derived by the above-described process can be separated from by-products (such as oligomeric or polymeric species and low molecular weight "fragments" from the fatty acid chains) by distillation. For example, the crude reaction product can be subjected to a distillation-separation at atmospheric or reduced pressure through a packed distillation column.

The decarboxylation-coupling product is often a wax at room temperature and pressure. In order to prevent clogging of the apparatus in which decarboxylation-coupling is performed, it may be necessary to heat those tubes by which the decarboxylation-coupling product is removed from the reaction zone and any vessel into which the ketone is to be collected.

The decarboxylation reaction can be conducted in the presence of at least one diluent. Suitable gaseous diluents may include nitrogen, hydrogen and carbon monoxide, carbon dioxide and $C_1$-$C_{18}$ aliphatic hydrocarbons. In certain circumstances, nitrogen and hydrogen have been shown to be useful diluents either in increasing the selectivity of the reaction to the particular products desired and/or in limiting catalyst degradation. When gaseous diluents are used, the fatty acid comprises from 1 to 95 mol % (e.g., from 5 to 50 mol %) of the fatty acid/carrier feed.

When a liquid diluent is employed, it would preferably be a good solvent for the starting materials, inert under reaction conditions, and easily separable from the ketone product. If separation by distillation is to be performed, the diluent can be a liquid that does not form an azeotropic mixture with the ketone and of which the boiling point is adequately separated from that of the ketone. Suitable liquid diluents include but are not limited to benzene, toluene, xylene, ethylbenzene, anisole, heptane, octane, nonane, decane, dodecane, dibutyl ether, and the like. When used, such liquid diluents comprise from 1 to 90 wt. % (e.g., from 5 to 50 wt. %), based on the total weight of the fatty acid and the diluent.

In some embodiments, improved yields and a high degree of selectivity in the ketonization reaction is obtained when the fatty acid is maintained in the vapor phase. Since condensation may occur in the pores of a solid catalyst even above the boiling point of the condensing fatty acid the operating temperature should preferably be kept sufficiently above the boiling point of the fatty acid to avoid or at least minimize pore condensation within the solid catalyst. In practice, we have found for an alumina catalyst this translates to the need to keep the reaction temperature above the condensation temperature or condensation point of the fatty acid or to keep the partial pressure of the fatty acid below the pressure at which it would condense into free liquid. However, the distance from the condensation point needed whether it is in terms of temperature above or pressure below condensation point can depend on the morphology and surface properties of the catalyst.

At a given pressure this condensation point avoidance may be accomplished by increasing the reaction temperature to a temperature above the condensation temperature of the fatty acid, as described. An alternative way to prevent condensation at a given pressure is to dilute the fatty acid with a diluent that may be a non-condensable at the reaction temperatures and pressures employed such as nitrogen, hydrogen, carbon monoxide, water, carbon dioxide, $C_1$-$C_{18}$ aliphatic hydrocarbon, and mixtures thereof. Moreover, another alternative is to operate the reactor at a lower pressure or even at reduced pressure below ambient pressure. In this aspect, we provide the vapor pressure of some representative straight chain saturated fatty acids as a function of temperature. (see, e.g., Anneken, D. J., Both, S., Christoph, R., Fieg, G., Steinberner, U. and Westfechtel, A., 2006, Fatty Acids. *Ullmann's Encyclopedia of Industrial Chemistry*, Vol. 14, 5th ed., pp. 73-112; VCH: Weinheim, Germany, at p. 79, FIG. 7).

IV. Distilling

In some embodiments, the step of distilling employs a distillation column to separate the ketones derived by the above-described process from by-products (such as oligomeric or polymeric species and low molecular weight "fragments" from the fatty acid chains). In some embodiments, the step of distilling preferably employs flash distillation or partial condensation techniques to remove by-products including at least low molecular weight "fragments".

Those of skill in the art will recognize that there is some flexibility in characterizing the high and low boiling fractions, and that the products may be obtained from "cuts" at various temperature ranges.

V. Hydrocracking

Hydrocracking is generally accomplished by contacting, in a hydrocracking reactor or reaction zone, the feedstock to be treated with a suitable hydrocracking catalyst under conditions of elevated temperature and pressure. Hydrocracking reactions reduce the overall molecular weight of the heavy feedstock to yield upgraded (that is, higher value) products including transportation fuels (e.g., diesel fuel), kerosene, and naphtha. These upgraded products that are converted in the hydrocracking reaction zone are typically separated from the total hydrocracker effluent as lower boiling fractions, using one or more separation and/or distillation operations. A remaining higher boiling fraction, containing heavy waxy products (referred herein as a "heavy hydrocarbon intermediate" or a "heavy waxy oil") suitable for upgrading to lubricating base oils by hydroisomerization to improve its cold flow properties, is typically isolated in the fractionators. The heavy waxy oil has a boiling range of approximately 343° C. to 704° C.

The temperature in the hydrocracking zone is within the range of from 260° C. to 482° C., typically within the range of from 316° C. to 427° C., more often with 343° C. to 399° C. A total pressure above 1000 psig (6.89 MPa) is used in the hydrocracking zone. For example, the total pressure can be above 1500 psig (10.34 MPa), or above 2000 psig (13.79 MPa). Although greater maximum pressures have been reported in the literature and may be operable, the maximum practical total pressure generally will not exceed 3000 psig (20.68 MPa). In some embodiments, more severe hydrocracking conditions such as higher temperature or pressure will result in producing an original base oil product with a higher viscosity index.

The LHSV generally falls within the range of from 0.1 to 50 h$^{-1}$, typically from 0.2 to 10 h$^{-1}$, more often from 0.5 to 5 h$^{-1}$. The supply of hydrogen (both make-up and recycle) is preferably in excess of the stoichiometric amount needed to crack the target molecules and generally falls within the range of from 500 to 10000 standard cubic feet (SCF)/barrel, typically from 1000 to 5000 SCF/barrel. Note that a feed rate of 10000 SCF/barrel is equivalent to 1781 L $_{H2}$/L feed. In general, hydrocracking conditions are sufficient to convert the ketone to hydrocarbon.

The catalysts used in the hydrocracking zone are composed of natural and synthetic materials having hydrogenation and dehydrogenation activity and cracking activity. These catalysts are well known in the art and are pre-selected to crack the target molecules and produce the desired product slate. Exemplary commercial cracking catalysts generally contain a support consisting of alumina, silica, silica-alumina composites, silica-alumina-zirconia composites, silica-alumina-titania composites, acid treated clays, crystalline aluminosilicate zeolitic molecular sieve (e.g., zeolite A, faujasite-Y, zeolite beta), and various combinations of the above. The hydrogenation/dehydrogenation components generally consist of a metal or metal compound of Group VIII or Group VIB of the Periodic Table of the Elements. Metals and their compounds such as, for example, Co, Ni, Mo, W, Pt, Pd and combinations thereof are known hydrogenation components of hydrocracking catalysts.

VI. Hydroisomerization Dewaxing

Heavy intermediate products are characterized by high pour points and high cloud points. In order to prepare commercially useful lubricating base oils from heavy intermediate products, the pour point and cloud point must be lowered without compromising the desired viscosity characteristics. Hydroisomerization dewaxing is intended to improve the cold flow properties of the heavy intermediate products by the selective addition of branching into the molecular structure. Hydroisomerization dewaxing ideally will achieve high conversion levels of the waxy oil to non-waxy iso-paraffins while at the same time minimizing cracking.

Hydroisomerization dewaxing is achieved by contacting a feed with a hydroisomerization dewaxing catalyst in a hydroisomerization zone under hydroisomerization dewaxing conditions. The hydroisomerization catalyst preferably comprises a shape selective intermediate pore size molecular sieve, a noble metal hydrogenation component, and at least a refractory oxide support. The shape selective intermediate pore size molecular sieve is preferably selected from the group consisting of SAPO-11, SAPO-31, SAPO-41, SM-3, SM-7, ZSM-22, ZSM-23, ZSM-35, ZSM-48, ZSM-57, SSZ-32, ferrierite, and combinations thereof. SAPO-11, SM-3, SM-7, SSZ-32, ZSM-23, and combinations thereof are often used. The noble metal hydrogenation component can be Pt, Pd, or combinations thereof.

The hydroisomerization dewaxing conditions depend on the feed used, the hydroisomerization dewaxing catalyst used, whether or not the catalyst is sulfided, the desired yield, and the desired properties of the product. Preferred hydroisomerization dewaxing conditions useful in the current invention include temperatures of 260° C. to 413° C.; a total pressure of 15 to 3000 psig (0.10 to 20.68 MPa); a LHSV of 0.25 to 20 h$^{-1}$; and a hydrogen to feed ratio from about 200 to 30000 SCF/barrel. In some embodiments, the hydrogen to feed ratio can be from 500 to 10000 SCF/barrel, in others from 1000 to 5000 SCF/barrel, and in still others from 2000 to 4000 SCF/barrel. Typically, hydrogen will be separated from the product and recycled to the hydroisomerization zone. In general, hydroisomerization dewaxing conditions are sufficient to convert ketones to hydrocarbon.

Additional details of suitable hydroisomerization dewaxing processes are described in U.S. Pat. Nos. 5,135,638; 5,282,958; and 7,282,134.

VII. Hydrofinishing

Hydrofinishing may be used as a step following hydroisomerization in the process of this invention to make base oils with improved properties. This step is intended to improve the oxidation stability, UV stability, and appearance of the product by removing traces of olefins and color bodies. A general description of hydrofinishing may be found in U.S. Pat. Nos. 3,852,207 and 4,673,487. In one embodiment, the isomerized product from the hydroisomerization reactor passes directly to the hydrofinishing reactor.

As used in this disclosure, the term UV stability refers to the stability of the lubricating base oil when exposed to ultraviolet light and oxygen. Instability is indicated when the lubricating base oil forms a visible precipitate or darker color upon exposure to ultraviolet light and air which results in a cloudiness or floc in the product. Usually lubricating base oils prepared by hydrocracking followed by hydroisomerization require UV stabilization before they are suitable for use in the manufacture of commercial lubricating oils.

The following terms will be used throughout the specification and will have the following meanings unless otherwise indicated.

The prefix "bio" refers to an association with a renewable resource of biological origin, such resources generally being exclusive of fossil fuels.

The phrase "Decarboxylation-coupling" refers to a chemical reaction in which two molecules, each having a carboxylic acid functional group, combine to form one single molecule having a ketone functional group, with concurrent loss of carbon dioxide and water.

The phrase "Decarboxylation-coupling zone" refers to a chemical reactor or apparatus suitable for Decarboxylation-coupling reactions.

The term "Base oil" refers to a hydrocarbon fluid to which other oils or substances are added to produce a lubricant.

The term "Lubricant," refers to substances (usually a fluid under operating conditions) introduced between two moving surfaces so to reduce the friction and wear between them. Base oils used as motor oils are generally classified by the American Petroleum Institute as being mineral oils (Group I, II, and III) or synthetic oils (Group IV and V). (See American Petroleum Institute (API) Publication Number 1509).

The phrase "Group I base oil" contain less than 90 percent saturates and/or greater than 0.03 percent sulfur and have a viscosity index greater than or equal to 80 and less than 120 using the ASTM methods specified in Table E-1 of American Petroleum Institute Publication 1509.

The phrase "Group II base oil" contain greater than or equal to 90 percent saturates and less than or equal to 0.03 percent sulfur and have a viscosity index greater than or equal to 80 and less than 120 using the ASTM methods specified in Table E-1 of American Petroleum Institute Publication 1509.

The phrase "Group III base oil" refers to a base oil which contains greater than or equal to 90% saturates and less than or equal to 0.03% sulfur and has a viscosity index greater than or equal to 120 using the ASTM methods specified in Table E-1 of American Petroleum Institute Publication 1509.

The term "Viscosity index" (VI) is an empirical, unit-less number indicating the effect of temperature change on the kinematic viscosity of the oil. The higher the VI of an oil, the lower its tendency to change viscosity with temperature. Viscosity index is measured according to ASTM D 2270-10.

The term "Pour point" is a measurement of the temperature at which a sample will begin to flow under certain carefully controlled conditions, which can be determined as described in ASTM D 5950-02 (reapproved 2007).

The term "Cloud point" represents the temperature at which a fluid begins to phase separate due to crystal formation, which can be determined as described in ASTM D 5771-10.

The term "fatty acid" refers to an aliphatic monocarboxylic acid having from 10 to 24 carbon atoms (e.g., from 12 to 22 carbon atoms, or from 14 to 18 carbon atoms). The term "aliphatic" means a straight (i.e., un-branched) or branched, substituted or un-substituted hydrocarbon chain that is completely saturated or that contains one or more units of unsaturation.

The term "conversion" refers to the amount of fatty acid in the feed that is converted to a compound other than fatty acid. Conversion is expressed as a mole percentage based on fatty acid in the feed. The conversion of fatty acid (FA) can be calculated from composition of feed and effluent streams using compositional data from analytical methods such as gas chromatography (GC) data using the following equation:

FA conv.(%)=100*[(mmol FA$_{(feed)}$−mmol FA$_{(effluent)}$)/ mmol FA$_{(feed)}$]

The term "Selectivity" refers to a mole percent based on converted fatty acid. It should be understood that each compound converted from fatty acid has an independent selectivity and that selectivity is independent from conversion. For example, if 50 mole % of the converted fatty acid is converted to ketone, the ketone selectivity is 50%. In some embodiments, the conversion is of fatty acid in the feed is at least 50%, (e.g., at least 60%, at least 70%, at least 80%, at least 90%, or at least 95%).

The term "condensation point" refers to a point in terms of temperature and pressure where a change occurs in the physical state of matter from the gaseous phase to the liquid phase.

The term "partial pressure" refers to (Dalton's Law of Partial Pressures, or Dalton's Law) the total pressure of a gas in a container being the sum of the partial pressures of the individual gases in the container.

The term "coupling" refers to a chemical reaction formed by two chemical subunits. For example, subunit A can couple to form A$_2$ and subunit A can couple with subunit B to form AB.

The term "LHSV" refers to (liquid hourly space velocity) =(volume of liquid feed at 60° F./hr)/volume of catalyst).

The Periodic Table of Elements referred to herein is the Table approved by IUPAC and the U.S. National Bureau of Standards, an example of which is the Periodic Table of the Elements by Los Alamos National Laboratory's Chemistry Division of October 2001.

For the purposes of this specification and appended claims, unless otherwise indicated, all numbers expressing quantities, percentages or proportions, and other numerical values used in the specification and claims, are to be understood as being modified in all instances by the term "about." Accordingly, unless indicated to the contrary, the numerical parameters set forth in the following specification and attached claims are approximations that can vary depending upon the desired properties sought to be obtained. It is noted that, as used in this specification and the appended claims, the singular forms "a," "an," and "the," include plural references unless expressly and unequivocally limited to one referent. As used herein, the term "include" and its grammatical variants are intended to be non-limiting, such that recitation of items in a list is not to the exclusion of other like items that can be substituted or added to the listed items. As used herein, the term "comprising" means including elements or steps that are identified following that term, but any such elements or steps are not exhaustive, and an embodiment can include other elements or steps.

EXAMPLES

The following examples are provided to demonstrate particular embodiments of the present invention. It should be appreciated by those of skill in the art that the methods disclosed in the examples which follow merely represent exemplary embodiments of the present invention. However, those of skill in the art should, in light of the present disclosure, appreciate that many changes can be made in the specific embodiments described and still obtain a like or similar result without departing from the spirit and scope of the present invention.

Examples 1-4

The ketonization of stearic acid over an alumina catalyst was conducted at conditions of 387° C., 1.0 h$^{-1}$ LHSV and 50 to 140 psig unit pressure to examine the effect of the partial pressure of stearic acid (P$_{SA}$) on ketone selectivity. Two diluents were used in the examples. Dodecane was added to improve the flow of the product mixture and further lower the partial pressure of the fatty acid. Nitrogen was also used to further lower the partial pressure of the fatty acid. The results are set forth in Table 1.

TABLE 1

| Example No. | Feed, wt % Stearic Acid in Dodecane | Pressure, psig | Pressure, psia | N$_2$ Flow Rate, ml/min | Partial Pressure, Stearic Acid, psia | Stearic acid conversion | Ketone selectivity |
|---|---|---|---|---|---|---|---|
| 1 | 50 | 90 | 104.7 | 50 | 20.7 | 80.00% | 33.50% |
| 2 | 25 | 50 | 64.7 | 25 | 7.6 | 92.80% | 47.80% |
| 3 | 25 | 50 | 64.7 | 100 | 4.1 | 84.00% | 74.50% |
| 4 | 25 | 140 | 154.7 | 300 | 4.3 | 95.40% | 90.10% |

The condensation point of stearic acid at 388° C. is about 25 psi. As shown, the ketone selectivity is improved if the partial pressure of the stearic acid is below about 5 psi or below about 20% of the pressure of condensation. Moreover, the conversion from gauge pressure to absolute pressure was calculated from psia=psig+14.7 psi.

Intuitively, it is surprising that the selectivity in a bimolecular reaction is favored relative to cracking reactions by lower partial pressure. At present the working hypothesis is that the formation of the ketone is a catalytic reaction happening on the catalyst surface whereas the formation of byproducts is caused by a competing parallel reaction that does not involve the catalyst initially, but forms unsaturated byproducts, which subsequently causes coke deposits and passivation of the catalyst. Conceivably, the byproduct forming side reaction is initiated by the formation of an anhydride of the fatty acid, which subsequently undergoes thermal decomposition to form the unwanted byproducts. Formation of a liquid phase will favor non-catalytic condensation reactions while limiting access of the fatty acid with the active sites on the catalyst where the ketonization reaction occurs.

All patents and publications referenced herein are hereby incorporated by reference to the extent not inconsistent herewith. It will be understood that certain of the above described structures, functions, and operations of the above described embodiments are not necessary to practice the present invention and are included in the description simply for completeness of an exemplary embodiment or embodiments. In addition, it will be understood that specific structures, functions, and operations set forth in the above-described referenced patents and publications can be practiced in conjunction with the present invention, but they are not essential to its practice. It is therefore to be understood that the invention may be practiced otherwise than as specifically described without actually departing from the spirit and scope of the present invention as defined by the appended claims.

What is claimed is:

1. A process for making an aliphatic ketone or a mixture of aliphatic ketones having about 14 to 52 carbon atoms, comprising: reaction of a fatty acid in a vapor phase with a decarboxylation-coupling catalyst in a decarboxylation-coupling zone, wherein a decarboxylation-coupling zone temperature is between about 20° C. to 100° C. above the condensation point of the fatty acid at the partial pressure of the fatty acid in the decarboxylation-coupling zone.

2. The process of claim 1, wherein the decarboxylation-coupling zone temperature is at least about 20° C., 25° C., 30° C., 35° C., 40° C., 45° C., 50° C., 55° C., 60° C. or 65° C. above the condensation point at the partial pressure of the fatty acid in the decarboxylation-coupling zone.

3. The process of claim 1, wherein the partial pressure of the fatty acid is between about 75 psia to 1 psia.

4. A process for making an aliphatic ketone or a mixture of aliphatic ketones having about 14 to 52 carbon atoms, comprising: reaction of a fatty acid in a vapor phase with a decarboxylation-coupling catalyst in a decarboxylation-coupling zone, wherein a partial pressure of the fatty acid is between 1% and 90% of the partial pressure at the condensation point at a given decarboxylation-coupling zone temperature.

5. The process of claim 4, wherein the decarboxylation-coupling zone temperature is between about 100° C. to 500° C.

6. The process of claim 4, wherein the partial pressure of the fatty acid is no more than 90%, 75%, 50%, 25%, 10%, 5% or 2% of the partial pressure at the condensation point at the given decarboxylation-coupling zone temperature.

7. The process of claim 1 or 4, wherein the partial pressure of the fatty acid is lowered relative to the pressure in the decarboxylation-coupling zone by the addition of an inert diluent selected from the group consisting of nitrogen, hydrogen, carbon monoxide, water, carbon dioxide, $C_1$-$C_{18}$ aliphatic hydrocarbon, and mixtures thereof.

8. The process of claim 1 or 4, wherein the decarboxylation-coupling catalyst is selected from the group consisting of alumina, supported metal carbonates, supported metal hydroxides, supported metal oxides, and combinations thereof.

9. The process of claim 1 or 4, wherein the fatty acid is selected from the group consisting of caproic acid, caprylic acid, capric acid, lauric acid, myristic acid, palmitic acid, stearic acid, arachidic acid, palmitolic acid, oleic acid, palm kernel oil acids, palm oil acids, coconut oil acids, soy bean oil acids, rape seed oil fatty acids, poultry fat derived fatty acids, beef tallow derived fatty acids, and combinations thereof.

10. The process of claim 1 or 4, further comprising a fatty acid conversion to the ketone of between about 70% to 100%.

11. The process of claim 1 or 4, further comprising a fatty acid conversion selectivity to the ketone of between about 30% to 100%.

12. The process of claim 1 or 4, further comprising a step of distilling, hydrocracking, hydroisomerization dewaxing, hydrofinishing, and combinations thereof.

13. The process of claim 1 or 4, further comprising a step of blending the aliphatic ketone or mixture of aliphatic ketones with a base oil selected from the group consisting of Group I oils, Group II oils, Group III oils, and combinations thereof to provide a lubricant composition.

* * * * *